(12) United States Patent
Goncalves (10) Patent No.: US 10,576,178 B2
(45) Date of Patent: Mar. 3, 2020

(54) STERILIZATION DEVICE USING HYDROGEN PEROXIDE AND OZONE VAPORIZED AND COMBINED THROUGH MULTIPLE CAPILLARY TUBES

(71) Applicant: Helder da Costa Goncalves, Boticas (PT)

(72) Inventor: Helder da Costa Goncalves, Boticas (PT)

( * ) Notice: Subject to any disclaimer, the term of this patent is extended or adjusted under 35 U.S.C. 154(b) by 340 days.

(21) Appl. No.: 15/521,498

(22) PCT Filed: Oct. 22, 2014

(86) PCT No.: PCT/PT2014/000064
§ 371 (c)(1),
(2) Date: Apr. 24, 2017

(87) PCT Pub. No.: WO2016/064288
PCT Pub. Date: Apr. 28, 2016

(65) Prior Publication Data
US 2017/0312378 A1 Nov. 2, 2017

(51) Int. Cl.
*A61L 2/00* (2006.01)
*A61L 9/00* (2006.01)
*A61L 2/20* (2006.01)
*B65B 55/18* (2006.01)

(52) U.S. Cl.
CPC .............. *A61L 2/202* (2013.01); *A61L 2/204* (2013.01); *A61L 2/208* (2013.01); *A61L 9/00* (2013.01); *B65B 55/18* (2013.01); *A61L 2202/24* (2013.01); *A61L 2202/25* (2013.01)

(58) Field of Classification Search
CPC .......... A61L 2/202; A61L 2/208; A61L 2/204; A61L 2202/25; A61L 2202/24

USPC .................... 422/28–29, 32–34, 292, 305
See application file for complete search history.

(56) References Cited

FOREIGN PATENT DOCUMENTS

| CA | 2 519 664 | 9/2005 | |
|----|-----------|--------|---|
| EP | 1 735 175 | 12/2006 | |
| EP | 1736175 A1 * | 12/2006 | ............... A61L 2/14 |
| EP | 1 764 115 | 3/2007 | |
| EP | 1 884 250 | 2/2008 | |
| PT | 2211917 | 7/2007 | |
| WO | WO2003/072150 | 9/2003 | |
| WO | WO2009/008755 | 1/2009 | |

* cited by examiner

*Primary Examiner* — Monzer R Chorbaji
(74) *Attorney, Agent, or Firm* — Varnum LLP (57) ABSTRACT

A process and device for the sterilization/disinfection with ozone and it is based on the hydrogen peroxide or other chemicals vapor injection that humidifies the load inside the chamber and transports the ozone through multiple capillaries into the chamber. Said Ozone sterilization or disinfection device with hydrogen peroxide vapor injection vaporizes and combines hydrogen peroxide or other chemicals with ozone in the capillaries in a vaporizer/mixer that feeds a sterilization/disinfection chamber, said feeding being made with a dose varying; the vaporizer/mixer working with a pressure between 0.0001 mbar and 3000 mbar absolute and heated by an automatic and/or electrical system, or by a micro-wave system at a temperature of 5° C. to 200° C.; the vaporization process being made to a sterilization/disinfection chamber at a pressure between 0.0001 mbar and 3000 mbar absolute is made drop by drop by capillary tubes, which transform the liquid into a pulverized gas combined with ozone.

16 Claims, 3 Drawing Sheets

STERILIZATION DEVICE USING HYDROGEN PEROXIDE AND OZONE VAPORIZED AND COMBINED THROUGH MULTIPLE CAPILLARY TUBES

The invention refers to a process and device for the sterilization/disinfection with ozone and it is based on the hydrogen peroxide or other chemicals vapor injection that humidifies the load inside the sterilization/disinfection chamber and transports the ozone through multiple capillaries into the vaporizer/mixer chamber. The precision of the humidification and the mixture is assured by controlling the introduction of liquids in the multiple capillaries in the vaporizer/mixer with drop by drop control, generating a powerful sterilizing/disinfecting agent into a heated sterilization/disinfection chamber with a temperature between 20° C. and 130° C. The process takes place in a chamber provided with one or two doors (with or without sanitary barrier) warmed at a temperature between 20° C. and 130° C. The decomposition of the sterilant/disinfectant is assured by a plasma generator with high voltage or other similar process that transforms the sterilizing/disinfecting gas into water, oxygen and free radicals when pumping it to the exterior of the chamber.

PREVIOUS INVENTIONS

Document WO 03072150 discloses a vapor generation unit which receives an aqueous hydrogen peroxide solution and includes a desiccant cartridge product.

Document EP1764115 describes a sterilization system which includes a hydrogen peroxide generator. It has a space for the introduction of the hydrogen peroxide in a treatment space and dehumidifier. It is important to note that there is a dehumidified air passage between the dehumidifier and the treatment space.

Document CA2519664 describes a sterilization process where the hydrogen peroxide solution is dripped from an injector into an evaporator during 3 minutes with a flow of 5 g/minute. The working chamber is filled with hydrogen peroxide after reducing the relative humidity in its interior to 1 to 10%. The sterilization occurs thanks to the hydrogen peroxide saturation inside the working chamber.

It is necessary to mention the technical documents in EP 06398011 application filed by the present applicant referring to a hydrogen peroxide sterilization process and device. According to that patent application, the extracted hydrogen peroxide from the chamber is burned thanks to a high tension inside a plasma generator, which may be part of the chamber.

The new patent application here presented is a result of development and improvement of the invention described in patent application EP 06398011.

We do also refer that this presented process is different than the process of the patent PCT/PT2007/000029 that is of the applicant's property. The state of the art and the studies made based on the above mentioned patent conduced to a multiple capillary vaporization device that uses different capillaries to introduce the hydrogen peroxide or other chemicals according to the characteristics of the cycles, to humidify the load inside the chamber and transport the ozone that is generated in an external generator into the chamber and to the material to be sterilized or disinfected.

This improvement results in precision of the drop by drop dosing in the vaporizer/mixer, with the introduction of capillary tubes of different dimensions that permit the usage of different concentrations of hydrogen peroxide or other chemicals and different quantities for humidification for each type of cycle, depending on the materials to be sterilized or disinfected. Humidification is transportation of the ozone to the materials to be sterilized or disinfected.

This new process has the capacity of obtaining the same sterilization/disinfection results as the previous patent PCT/PT2007/000029, but better precision in the drop by drop dosing system as in this new system multiple capillaries are used whereas in the previous system only one capillary was used. In the previous patent sterilization was reached with hydrogen peroxide. In this new process the multiple capillaries permit recombining lower concentrations of hydrogen peroxide or other chemicals in the vaporizer/mixer that will be sterilizing/disinfecting agent in this new device, obtaining the same results as in the previous patented device. This process permits the combination of different chemical products to obtain a sterilizing/disinfecting agent.

The presented process also includes an adjustable fixed dose system from where the air is removed before the vaporization starts. The referred adjustable dose quantity may be adjusted previously.

The sterilization or disinfection process with the new device is less corrosive in contact with materials, especially with flexible endoscopes as lower concentrations and quantities of hydrogen peroxide get in contact with the materials.

Advantages of the Device of the Present Invention:

The drop by drop vaporization device has advantages compared to the existing ones, as the precision obtained with the chemical products, dripping, using capillary tubes in the vaporizer that mix and control the doses variability is applied through a computerized control system. A computer monitors and controls permanently the humidification that is made with the chemical products and the functioning of the device through various pressure and/or temperature and/or humidity and/or concentration sensors.

The vaporizer/mixer (4G) vaporizes 0.01 ml-1000 ml of liquid chemical products through the capillary tubes (4D). During this phase, in order to create a humid atmosphere, several electric valves (4E, 4H, 13A and 13E) open for controlled introduction of ozone mixed with other chemical products such as hydrogen peroxide, acetic acid, peracetic acid, water, formaldehyde or formaldehyde with water, or other chemical products which actuate on DNA or RNA level, either the products themselves or combined between them, or for controlled introduction of chemical products such as hydrogen peroxide, acetic acid, peracetic acid, water, formaldehyde or formaldehyde with water, or other chemical products which actuate on DNA or RNA level, either the products themselves or combined between them without ozone, or for the controlled introduction of propylene oxide combined with water or ethylene oxide combined with water, in the vaporizer/mixer that is then aspirated from the vaporizer/mixer (4G) to the sterilization chamber (1). It shall be understood that the chemical products referred above will be used in their own combination as commercialized in the market.

Concerning the injection, the injection device does not have a syringe injector but a set of capillary tubes inside the vaporizer, which transform liquid into humid pulverized gas and mix it with ozone or other chemical products, creating a sterilizing/disinfecting agent. Heat created through heating elements or microwave system can be used as heat source for the vaporization. The vaporization may also be improved by an ultra-sound system applied to the capillary tubes.

With this capillary system, high precision in liquid dripping is obtained, permitting the usage of low concentration hydrogen peroxide. This system may use hydrogen peroxide (or other chemical products combinations) as humidifying agent with concentrations between 90% and 40%, 40% and 30%, 30% and 20%, 20% and 10%, 10% and 5%, 5% and 1% depending on the set of capillaries applied on the vaporizer/mixer.

It is possible to associate an adjustable fixed dose system (13B) to one of the capillary tubes. After the refilling of the adjustable dosing (13B) the valves (13A) are closed and the liquid inside the adjustable dosing (13B) is conducted to the vaporizer/mixer (4G) through the capillary tube (4D) by the opening of the vaporizer entry valve (13E).

Occurs after the pressure within the vaporizer reaches less than 100 mbar in the vaporizer/mixer (4G) in the case of a sterilization process, or the atmospheric pressure in case of a disinfection process.

The vaporizer/mixer (4G) of this invention is physically open to the sterilization/disinfection chamber (1); there is no valve between the vaporizer/mixer (4G) and the chamber. Control is done through vaporizer entry valves (4E,13E) at the entrance of the capillaries applied on the vaporizer/mixer which are controlled by a computer based on the values measured by the various sensors (4B);

In the invented device, the vaporizer/mixer (4G) and the dosing system themselves, are able to vaporize the chemical mixture for room disinfection (room or chamber). Control is based on environment temperature and/or relative humidity and on the concentration of chemicals in the environment;

The control system is based on the pressure and/or relative humidity and/or temperature of the sterilization/disinfection chamber, the injected quantity of ozone or mixture of chemical products into the sterilization/disinfection chamber, controlling the number of openings of the vaporizer/mixer valves (4E, 4H and 13E) of the capillaries (4D) that carry the ozone and mixture of chemical products. It is produced a mixture that interacts with the temperature inside the chamber to obtain sterilization/disinfection; The quantity of ozone that is placed inside the chamber causes a chamber pressure variation of 0 mbar-10 mbar, 10 mbar-100 mbar, 100 mbar-200 mbar, 200 mbar-500 mbar, 500 mbar-800 mbar, depending on the type of cycle, on the capillaries used and on the mixture of chemical products used;

DESCRIPTION OF THE DRAWINGS

The invention is now described as a non-limitative example with reference to the attached drawings:

1—Sterilization/disinfection chamber
1A—Chamber heater
1B—Chamber sensors
2—Clean side door
2A—Clean side door heater
2B—Clean side door sensor
3—Unclean side door
3A—Unclean side door heater
3B—Unclean side door sensor
4—Vaporizer/Mixer
4A—Vaporizer/Mixer heater
4B—Vaporizer/Mixer sensors
4C—Filters
4D—Capillary tubes
4E—Vaporizer/Mixer entry valve
4F—PTFE connection
4G—Vaporizer/Mixer chamber
4H—Vaporizer/Mixer entry valve for Ozone
4I—Ultra-sound system
4J—Micro-wave system
5—Dosing peristaltic pump
6—Chemical product tank
6A—Level sensor
6B—Level float
6C—Tank sensor
6D—Temperature controller unit
6E—Peltier plate
6F—Tank
7—Filling peristaltic pump
8—Supply system
8A—Drawer
8B—Recognition sensor
8C—Perforation cylinder
8D—Perforation needle
8E—Drawer cylinder
8F—Sterilizing agent Bottle/Container with recognition system
8G—Recharge Bottle/Container holder
9—Plasma generator unit
9A—High voltage unit
9B—Exhaust valve
9C—Plasma generator chamber
9D—High voltage electrodes
9E—Temperature sensor
10—Vacuum assembly with controlled temperature and heating/cooling system
10A—Vacuum pump
10B—Oil separator
10C—Odor filter
10D—Condenser
10E—Air valve
10F—Air inlet
10G—Control unit
10H—Oil pump
10I—Heat dissipater
10J—Ventilator/Fan
10L—Liquid exhaustion
10M—Sensors
10N—Exhaustion heating
10O—Liquids deposit
10P—Motor
10Q—Membrane
11A—Ventilation valve
11B—Ventilation filter
11C—Transducer
12—Ozone generator unit
12A—Connection of Ozone to the Vaporizer
12B—Ozone generator
12C—Air entry Filter
12D—Control Board
12E—Electrical Connection
13—Adjustable fixed dose system 13A—Adjustable dosing valve
13B—Adjustable dosing
13C—Filter
13E—Vaporizer/Mixer entry valve
FIG. 1b shows in detail the components of the Supply system. The components are identified by signs as follows:
8A—Drawer
8B—Recognition sensor
8C—Perforation cylinder
8D—Perforation needle
8E—Drawer cylinder
8G—Recharge Bottle/Container holder
8H—Control Board

DETAILED DESCRIPTION

Figure 1A:
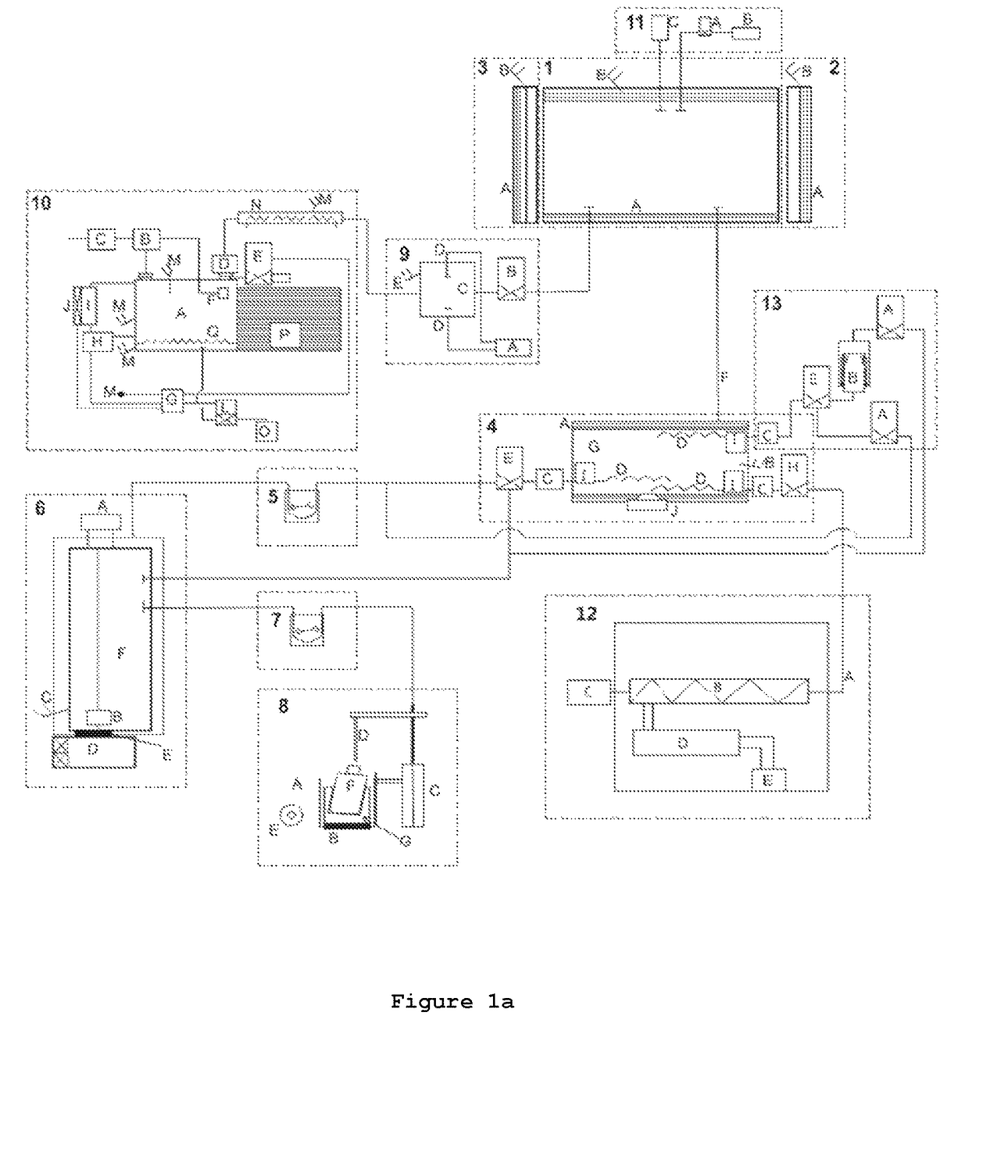
FIG. 1a shows a device scheme drawing which allows accomplishing the sterilization/disinfection process according to the invention. In this figure the components of the device of the present invention are identified by reference signs as follows.

Referring to FIG. 1a, the supply system (8) (showed in more detail in FIG. 1b) is composed by a drawer (8A), a recharge recognition sensor (8B), a perforation cylinder (8C), a needle (8D), a drawer cylinder (8E), a recharge bottle/container (8F) including RFID, TAG or microchip, a bottle/container holder (8G) and a control board (8H). The drawer where the chemical product recharge is placed works with a manual or mechanical system or an electric and/or pneumatic cylinder mechanism (8E), after recognizing the recharge through RFID, TAG or microchip identification. After the recognizing of the recharge, the automation system prints the recharge data through the system printer and/or saves the data in the system computer.

Figure 1B:
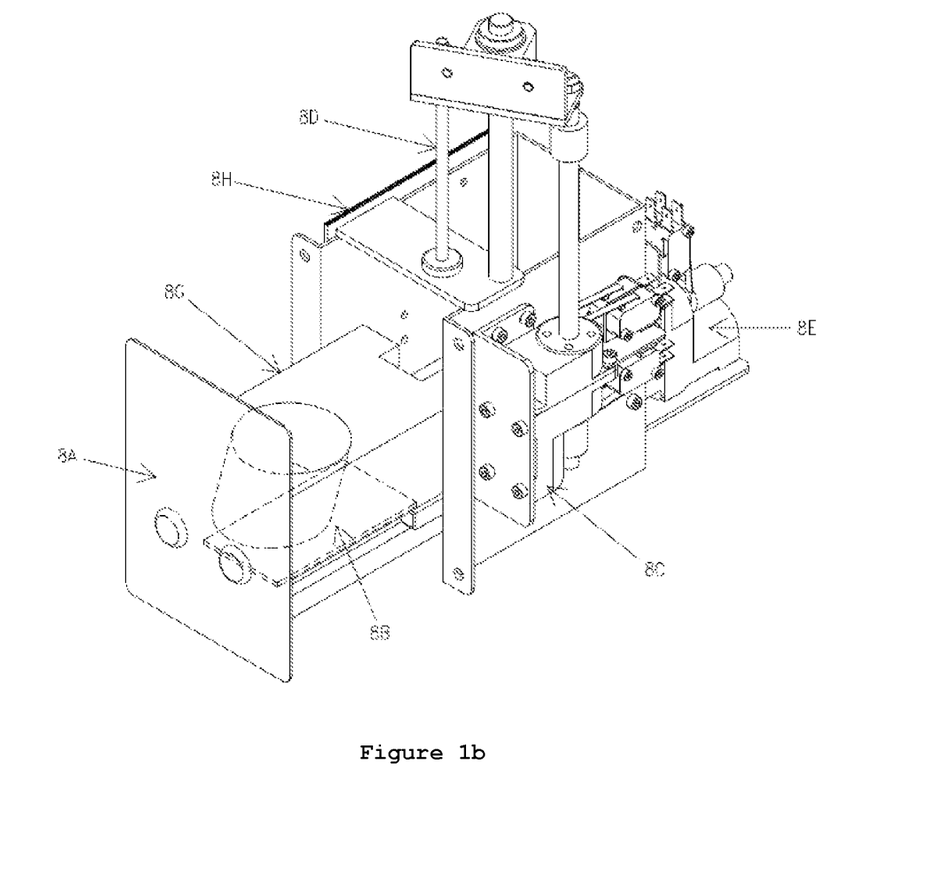

After indication in the system screen of lack of liquid in the tank (6F) an order from the operator starts the refilling sequence. The drawer (8A) opens and the operator gets the warning in the screen to remove the recharge bottle/container cap before placing it in the holder (8G) which has been designed in a way to keep the bottle/container (8F) in an inclined position allowing the perforation needle (8D) to reach the bottom of the bottle/container (8F) to remove the whole quantity of liquid.

The recognition sensor (8B) installed under the bottle/container holder (8G) reads the RFID, TAG or microchip and accepts the chemical product recharge, which is used according to the manufacturer's instructions assuring efficient sterilization/disinfection cycles.

After the recharge has been recognized and validated, the drawer (8A) is closed and the needle (8D) perforates the recharge. This needle works thanks to a manual and/or mechanical and/or electrical and/or pneumatic system (8C). After the perforation of the bottle/container and/or other, the chemical product is pumped by the filling pump (7) and placed into a tank (6F), which has controlled temperature between −10° C. and 30° C., by an assembly of ventilator and peltier plate (6D and 6E).

The chemical product is removed from a tank (6F) thanks to a dosing pump (5); the liquid passes through one of the three way vaporization valves (4E, 13A or 13E) and returns to the tank for air removal of the tubes. Afterwards it introduces the chemical product into one of the vaporizer's/mixer's capillary tubes (4D). The ozone enters the vaporizer/mixer through the valve (4H) connected to a capillary (4D) and is combined with the chemical product. The mixture is then diffused to the sterilization/disinfection chamber (1). The chemical product tank (6F) is provided with a system that controls the float (6B) and interacts with the computer or the control unit, in order to prevent the cycles to initiate without chemical product in the tank. The level of the chemical product is controlled by the level or pressure sensor (6A) which sends the information to the computer.

This process also includes an adjustable dose system (13) that allows the adjustment of a defined dose of a certain chemical product. When the vaporizer entry valve (13E) is used, the computer system gives indication to the dosing peristaltic pump (5) to start pumping the chemical product from a tank (6F). The adjustable dosing valves (13A) open. The liquid passes upward through these valves to the adjustable dosing (13B) during a period of time until the complete removal of air from the inside of the adjustable dosing is guaranteed. After that period, the adjustable dosing valves (13A) are closed and the dosing peristaltic pump (5) stops. Then the vaporizer/mixer entry valve (13E) starts pulsing controlled by the computer system through the information of pressure and/or temperature and/or humidity and/or concentration given by the vaporizer/mixer sensors (4B), and introduces the chemical product into the vaporizer/mixer (4G) drop by drop through the capillary tube (4D).

The vaporization and combination of the chemical product agent drop by drop with ozone is obtained by a new device which includes vaporizer/mixer (4G), heated by an automatic and/or electrical heating system (4A), and/or by a micro-wave system (4J), and capillary tubes (4D) in its interior, which are calibrated and adjusted to the type of cycle to be developed. The humidifying liquid is fed through a dosing pump (5).

As the vaporization is drop by drop for humidification that is combined with the ozone, it is possible to dose small vapor quantities of the mixture/combination from the vaporizer chamber (4G) to the sterilization/disinfection chamber (1) and it is controlled by the openings of the valves (4E, 4H and 13E).

With said mixture/combination and vaporization method it is possible to sterilize/disinfect material packed in cellulose-based common paper, per se or made of synthetic fibers, besides the polypropylene, polyethylene or polyethylene-based packaging products or other plastic fibers for sterilization packaging.

The process is developed inside a sterilization/disinfection chamber (1) provided with one or two doors (with or without sanitary barrier) heated between 20° C. and 130° C. in order to achieve a biological kill inside a "PCD" composed by a flexible tube of 15 meters length with a diameter of 1 mm with place for biological indicators in the middle of the length, or inside rigid stainless steel tubes of less than 5000 mm length and a diameter above 0.5 mm.

This vaporizer/mixer is essentially based on a chamber (4G)—provided with a heating system (4A and/or 4J)—that has a programming command, in order to control the opening/closing of the vaporizer/mixer entry valves (4E, 4H and 13E) after the continuous pressure and/or humidity and/or temperature and/or mixture concentration calculation. Between the chemical products' entry valves (4E or 13E) and the vaporizer/mixer chamber (4G) there is a capillary tube (4D) designed for the drop by drop vaporization. The dosing is ensured by electrical valves (4E, 4H) at the entry of the capillary tubes (4D) of the vaporizer/mixer, controlled by a computer or control unit. In case of using the adjustable dosing (13B), the dosing is not done by the valve (13E) but by the total quantity of liquid inside the adjustable dosing (13B).

After being heated by the vaporizer/mixer (4G) the capillary tubes (4D) are able to vaporize the chemical products combination drop by drop creating a sterilizing/disinfecting combination. The process is controlled and programmed by the computer.

The vaporizer/mixer (4G) is heated by an automatic and/or electrical heating system (4A), and/or by a microwave system (4J) applied to the vaporizer chamber, at a temperature between 5° C. and 200° C. An ultra-sound system (4I) applied to the capillary tubes can also be used to improve the vaporization. The vaporizer/mixer (4G) has pressure and/or temperature and/or humidity and/or concentration sensors (4B) which send the information to the control computer. The chemical product is injected drop by drop into the vaporizer/mixer (4G) and is combined with ozone that also enters the vaporizer/mixer (4G) through a capillary tube (4D) controlled by an electric valve (4H).

The vaporizer/mixer is mechanically connected to the sterilization/disinfection chamber (1) by a clamp system with a PTFE tube (4F) which conveys the combination of chemical products in gas state to the sterilization/disinfection chamber (1) in the best conditions.

Between the dosing pump (5) and the vaporizer/mixer valves (4E, 13A and 13E) there is a return line of the chemical product to remove the air from the tubing of the injection circuit of the chemical product in the drop by drop vaporizer/mixer (4G). A filter (4C) will assure that particles or residues do not reach the capillary tube (4D).

Near the exhaust valve (9B) of the chamber (1), there is an air removing system thanks to a vacuum pump (10A), which removes the air before starting the drop by drop injection in the vaporizer/mixer (4G). The gas that comes out of the sterilization/disinfection chamber (1) passes through a plasma generator (9C) with high voltage electrodes (9D), which catalyzes the mixture of the chemical product and ozone at the chamber exit, breaking the combination into water, oxygen and free radicals by a plasma effect. The plasma generator can be an integral part of the chamber or not. In the case that flammable chemical products are used, a liquid ring vacuum pump will be used.

The sterilization/disinfection chamber (1) and doors (2 and 3) have pressure and/or temperature and/or humidity and/or concentration sensors (11C and 1B, 2B, 3B) which inform the computer that controls the process.

According to FIG. 1a, in order to achieve a drop by drop injection, the capillary tubes (4D) have a length between 5 mm and 5500 mm with a hole between 1 μmm and 10 mm, which allows the drop by drop vaporization with the necessary precision for the combination of chemical products. The entry valves (4E, 4H and 13E) are controlled based on the value vaporized in each opening. There will be successive openings of the valve until reaching the established pressure value between 0.0001 mbar and 3000 mbar ABS inside the sterilization/disinfection chamber.

The dosing system has no air, which means that if there is less material inside the chamber for the same value of pressure, it will be necessary to inject less sterilizing/disinfecting agent. On the other hand, if there is more material inside the chamber for the same pressure value, it will be necessary to inject more sterilizing/disinfecting agent. This occurs due to the possible condensation of the sterilizing/disinfecting agent inside the chamber. Before initiating the injection the load inside the chamber is previously heated.

The sterilization/disinfection is reached for example in lumens with 15 meters length and 1 mm diameter with biological indicators containing *Geobacillus Stearothermophilus* inserted inside the lumen in a population of $\geq 1.0 \times 10^6$ during the diffusion period between 10 and 12.000 seconds.

The drop by drop dosing system is ensured by a peristaltic pump (5)—or other—between the chemical product tank (6F) and the vaporizer/mixer (4G) that starts the pumping in periods of 1 to 855 seconds before the injection, in order to remove all the air in the tubes. After this pumping period, and air removal from the tubes, the vaporizer/mixer valves (4E and 13E) open with intermittent openings controlled by the pressure and/or temperature and/or humidity and/or concentration read in the sterilization/disinfection chamber (1).

Figure 2:
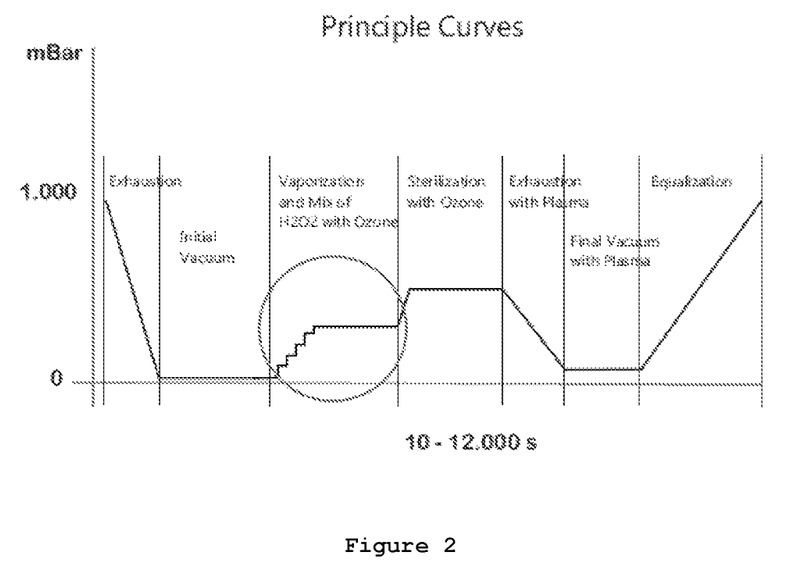
FIG. 2 is a graph depicting the principle of the functioning of the device with the pressure evolution in the vaporizer depending on the time.

With this process, there is a curve of vaporization with an entry similar to the one shown in FIG. 2. The diffusion period occurs between 10 and 12000 seconds with a pressure between 0.0001 mbar and 3000 mbar ABS until having the right quantity of chemicals combination in the chamber, initiating the sterilization/disinfection with a time frame of 10 to 12000 seconds.

The device of the present invention is also appropriate for the sterilization and/or disinfection of stomatology material in a chamber of reduced size, endoscopes and videoscopes, cork stoppers commonly used in wine bottles, laminated cork and cork combined with other products, among others.

This device also presents Penetration Test cycle of the sterilizing/disinfecting agent and a cycle of Leak Test, which can be independent or simultaneous.

This device also performs functions of a RESISTOMETER for evaluating biological and/or chemical indicators for laboratory studies of biological kill using as sterilizing/disinfecting agent ozone combined with hydrogen peroxide, acetic acid, peracetic acid, water, formaldehyde or formaldehyde with water, or other chemical products which actuate on DNA or RNA level, either the products themselves or combined between them, or chemical products such as hydrogen peroxide, acetic acid, peracetic acid, water, formaldehyde or formaldehyde with water, or other chemical products which actuate on DNA or RNA level, either the products themselves or combined between them without ozone, or propylene oxide combined with water or ethylene oxide combined with water (it shall be understood that the chemical products referred above will be used in their own combination as commercialized in the market).

The advantage of the multi-capillary vaporizer/mixer is that it can recombine different products with precision to obtain sterilization/disinfection or ambient disinfection when applied to be used at atmospheric pressure. It is capable to mix/combine hydrogen peroxide and ozone resulting in the capacity of using low concentrations of hydrogen peroxide or others, which lowers corrosiveness of the sterilizing/disinfecting agent inside the chamber, turning this process environment friendly maintaining the efficiency and not damaging the instruments to be sterilized or disinfected.

On the other hand the low concentration of the chemicals permits its optimization in each cycle and improves the decomposition of the chemicals in the plasma generator (9C). After the chemicals pass through a molecular sieve (10C) so that there is less than 1 ppm at the output of the exhaustion.

Modifications can be made to the disclosed sterilization/disinfection device, maintaining the functioning principle in the attached claims, for example modifications with equivalent elements, which are contained in the scope of this invention.

Besides, other chemical products may be combined with the ones claimed in this patent application.

The invention claimed is:

1. Ozone sterilization or disinfection device with chemical products vapor injection wherein said device vaporizes and combines ozone with hydrogen peroxide, acetic acid, peracetic acid, water, formaldehyde or formaldehyde with water, or other chemical products suitable for sterilization or disinfection through multiple capillary tubes (4D) in a vaporizer/mixer (4G) that feeds a sterilization/disinfection chamber (1), said feeding being made with a dose varying depending on the control performed by a computer or control unit, or being made with an adjustable dosing unit (13B); the vaporizer/mixer starts working with a pressure inferior to the atmospheric pressure and heated by an automatic and/or electrical system (4A), or by a micro-wave system (4J) at a temperature of 5° C. to 200° C.; the vaporization process being made in vacuum or at atmospheric pressure to a sterilization/disinfection chamber (1) at a pressure between 0.0001 mbar and 3000 mbar absolute; the filling of the chemical product, supplied from a tank (6F) is made drop by drop by capillary tubes (4D) with controlled temperature, which transform the liquid into a pulverized gas; the computer controlling electrical valves (4E and 4H) following the dosing pump (5) and ozone generator (12B) which includes a control board (12D) and an air entry filter (12C), using information concerning the pressure and/or temperature and/or humidity and/or concentration given by the sensors (1B, 2B, 3B, 4B and 11C), being the pressure inside the sterilization/disinfection chamber (1) maintained at a constant predefined value during the vaporization and sterilization or disinfection process; said device also comprising a vacuum pump (10A) which includes an exhaustion heating system (10N) and a temperature control sensor (10M) and an air valve heating system (10E) and a cooling system composed by an oil pump (10H) a heat dissipater (10I) a fan (10J) and an electronic control unit (10G), and also comprises a membrane (10Q) that separates the water from the oil, a liquid exhaustion system (10L), a liquids deposit (10O), an oil separator (10B) with connection to the air inlet (10F), and a molecular sieve (10C) with a capacity between 0.5-5 L; at the exhaustion phase a plasma generator (9C) is activated to generate plasma by high voltage (9A) applied to the electrodes (9D), the temperature of the plasma generator being monitored by sensors (9E); the device comprising an automatic supplying system that removes the sterilizing agent from the bottle/container (8F) which is inserted in a holder (8G) that keeps said device in an inclined position that allows the perforation needle (8D) which is moved by a servo-motor (8C) to reach the bottom of the bottle/container and thereby remove the whole liquid, the drawer (8A) having a recharge recognition sensor (8B) that recognizes the recharge by RFID, TAG or microchip, and sends the recharge data to a PC that will be printed after the refilling, is automatically moved by a servo-motor (8E); the refilling system enabling the supplying of different chemical products that will be automatically recognized and pumped to the corresponding tank.

2. The Device according to claim 1, wherein vaporization can be increased by an ultra-sound system (4I) at the entry of the capillary tubes (4D), or a micro-wave system (4J) applied to the vaporizer chamber (4G).

3. The Device according to claim 1, wherein said device comprises pressure and/or temperature and/or humidity and/or concentration sensors, namely in the vaporizer/mixer (4G), in the tank of the chemical product (6F) and in the sterilization/disinfection chamber (1); and having an ozone generator (12B) and the ozone being combined in the vaporizer/mixer (4G) through the capillaries and injected into the chamber.

4. The device according to claim 1, wherein the vaporizer/mixer (4G) is mechanically connected to the sterilization/disinfection chamber (1) by a clamp system and a PTFE tube.

5. The device according to claim 1, wherein the sterilization/disinfection chamber (1) comprises a vacuum pump (10A).

6. The device according to claim 1, wherein said device comprises an air removing system, near the entry valves (4E and 13E) of the vaporizer, through a tube returning to the tank (6F) controlled by the computer system.

7. The device according to claim 1, wherein said device comprises a molecular sieve (10C) at the end of an exhaustion line for retaining any eventual residues.

8. The device according to claim 1 wherein said device comprises multiple capillary tubes (4D) with a length between 5 mm and 5500 mm, with an orifice between 1 µmm to 10 mm.

9. A sterilization method performed on the ozone sterilization or disinfection device with chemical products vapor injection wherein said device vaporizes and combines ozone with hydrogen peroxide, acetic acid, peracetic acid, water, formaldehyde or formaldehyde with water, through multiple capillary tubes (4D) in a vaporizer/mixer (4G) that feeds a sterilization/disinfection chamber (1), said feeding being made with a dose varying depending on the control performed by a computer or control unit, or being made with an adjustable dosing unit (13B); the vaporizer/mixer starts working with a pressure inferior to the atmospheric pressure and heated by an automatic and/or electrical system (4A), or by a micro-wave system (4J) at a temperature of 5° C. to 200° C.; the vaporization process being made in vacuum or at atmospheric pressure to a sterilization/disinfection chamber (1) at a pressure between 0.0001 mbar and 3000 mbar absolute; the filling of the chemical product, supplied from a tank (6F) is made drop by drop by capillary tubes (4D) with controlled temperature, which transform the liquid into a pulverized gas; the computer controlling electrical valves (4E and 4H) following the dosing pump (5) and ozone generator (12B) which includes a control board (12D) and an air entry filter (12C), taking into account the information concerning the pressure and/or temperature and/or humidity and/or concentration given by the sensors (1B, 2B, 3B, 4B and 11C), being the pressure inside the sterilization/disinfection chamber (1) maintained at a constant predefined value during the vaporization and sterilization or disinfection process; said device also comprising a vacuum pump (10A) which includes an exhaustion heating system (10N) and a temperature control sensor (10M) and an air valve heating system (10E) and a cooling system composed by an oil pump (10H) a heat dissipater (10I) a fan (10J) and an electronic control unit (10G), and also comprises a membrane (10Q) that separates the water from the oil, a liquid exhaustion system (10L), a liquids deposit (10O), an oil separator (10B) with connection to the air inlet (10F), and a molecular sieve (10C) with big a capacity between 0.5-5 L; at the exhaustion phase a plasma generator (9C) is activated to generate plasma by high voltage (9A) applied to the electrodes (9D), the temperature of the plasma generator being monitored by sensors (9E); the device comprising an automatic supplying system that removes the sterilizing agent from the bottle/container (8F) which is inserted in a holder (8G) that keeps said device in an inclined position that allows the perforation needle (8D) which is moved by a servo-motor (8C) to reach the bottom of the bottle/container and remove the whole liquid, the drawer (8A) having a recharge recognition sensor (8B) that recognizes the recharge by RFID, TAG or microchip, and sends the recharge data to a PC that will be printed after the refilling, is automatically moved by a servo-motor (8E); the refilling system enabling the supplying of different chemical products that will be automatically recognized and pumped to the corresponding tank, wherein the vaporizer/mixer (4G) vaporizes about 0.01-1000 ml of hydrogen peroxide or other chemicals suitable for sterilization or disinfection, either from one of the tanks (6F) or from the adjustable dosing (13B), combined with ozone for a period of about 1-1000 seconds, which is injected to a sterilization/disinfection chamber (1) where the pressure evolves to values of about 0.0001 to 3000 mbar absolute.

10. The sterilization method according to claim 9, wherein the hydrogen peroxide or other chemicals suitable for sterilization or disinfection vapor recombined with ozone injection into the sterilization/disinfection chamber (1) occurs in temperature values between 20° and 130° C., after the vaporizer/mixer (4G) being heated by an automatic and/or electrical heating system (4A) or micro-wave system (4J) to a temperature between 5° C. and 200° C.

11. The sterilization method according to claim 9, wherein the hydrogen peroxide or other chemicals suitable for sterilization or disinfection being injected drop by drop into the vaporizer/mixer (4G), creating a humid atmosphere mixed with ozone, which leads the mixture in a gas state to the sterilization/disinfector chamber (1), comprising a vacuum pump (10A) to extract the air from the chamber (1) and vaporizer/mixer (4G) before the drop by drop injection being initiated in the vaporizer/mixer (4G) and before the ozone injection through the vale (4H), diffusing said hydrogen peroxide or other chemicals suitable for sterilization or disinfection in the sterilization/disinfection chamber (1).

12. The sterilization method according to claim 9 wherein the exhaustion of the mixture that is inside the sterilization/disinfection chamber (1) passes through a heated tube (10N) and is made by a vacuum pump (10A) which has a heating system by an air valve (10E), and a cooling system by a set of heat dissipater (10I) a ventilator/fan (10J) and an oil pump (10H), as well as a removal system of aqueous liquids by a membrane (10Q) a liquid's exhaustion valve (10L) and a control unit (10G) that deposits the aqueous liquids in a deposit (10O); while removing the hydrogen peroxide or other chemicals suitable for sterilization or disinfection mixed/combined with ozone from the chamber (1) they pass through the plasma generator (9C) with high voltage electrodes (9D), breaking the hydrogen peroxide or other chemicals suitable for sterilization or disinfection mixed and ozone into water, oxygen and free radicals due to the plasma effect.

13. The sterilization method according to claim 9, wherein the multiple capillary tubes (4D) inject the hydrogen peroxide or other chemicals suitable for sterilization or disinfection mixed drop by drop into the vaporizer/mixer (4G) and inject ozone, being the liquid that passes the capillaries controlled by vaporizer entry valves (4E and 13E); said valves being controlled based on the value of the vaporized mixture/combination in each opening, having successive opening of valves (4E and 13E) until the established value has been vaporized to obtain a pressure between 0.0001 mbar and 3000 mbar absolute and being capable of vaporizing ozone with chemical products, comprising: hydrogen peroxide, acetic acid, peracetic acid, water, formaldehyde or formaldehyde with water, or other chemical products suitable for sterilization or disinfection.

14. The sterilization method according to claim 9, wherein the method includes a Penetration Test cycle of the chemicals' combinations, a cycle of Leak Test, a cycle that incorporates the Penetration Test and the Leak Test in a single cycle, a cycle for flexible endoscopes which is controlled by the automation system in a way that the PLC manages the pressure variation and keep the pressure variation within the limits that the endoscopes withstand, thereby reducing the pressure variation between the internal and external parts of the endoscopes, and cycles dedicated to different materials, based on the different capillaries in the vaporizer/mixer and the different capillary tubes.

15. A method of use of an ozone sterilization or disinfection device with chemical products vapor injection wherein said device vaporizes and combines ozone with hydrogen peroxide, acetic acid, peracetic acid, water, formaldehyde or formaldehyde with water, through multiple capillary tubes (4D) in a vaporizer/mixer (4G) that feeds a sterilization/disinfection chamber (1), said feeding being made with a dose varying depending on the control performed by a computer or control unit, or being made with an adjustable dosing unit (13B); the vaporizer/mixer starts working with a pressure inferior to the atmospheric pressure and heated by an automatic and/or electrical system (4A), or by a micro-wave system (4J) at a temperature of 5° C. to 200° C.; the vaporization process being made in vacuum or at atmospheric pressure to a sterilization/disinfection chamber (1) at a pressure between 0.0001 mbar and 3000 mbar absolute; the filling of the chemical product, supplied from a tank (6F) is made drop by drop by capillary tubes (4D) with controlled temperature, which transform the liquid into a pulverized gas; the computer controlling electrical valves (4E and 4H) following the dosing pump (5) and ozone generator (12B) which includes a control board (12D) and an air entry filter (12C), taking into account the information concerning the pressure and/or temperature and/or humidity and/or concentration given by the sensors (1B, 2B, 3B, 4B and 11C), being the pressure inside the sterilization/disinfection chamber (1) maintained at a constant predefined value during the vaporization and sterilization or disinfection process; said device also comprising a vacuum pump (10A) which includes an exhaustion heating system (10N) and a temperature control sensor (10M) and an air valve heating system (10E) and a cooling system composed by an oil pump (10H) a heat dissipater (10I) a fan (10J) and an electronic control unit (10G), and also comprises a membrane (10Q) that separates the water from the oil, a liquid exhaustion system (10L), a liquids deposit (10O), an oil separator (10B) with connection to the air inlet (10F), and a molecular sieve (10C) with big a capacity between 0.5-5 L; at the exhaustion phase a plasma generator (9C) is activated to generate plasma by high voltage (9A) applied to the electrodes (9D), the temperature of the plasma generator being monitored by sensors (9E); the device comprising an automatic supplying system that removes the sterilizing agent from the bottle/container (8F) which is inserted in a holder (8G) that keeps said device in an inclined position that allows the perforation needle (8D) which is moved by a servo-motor (8C) to reach the bottom of the bottle/container and thereby remove the whole liquid, the drawer (8A) having a recharge recognition sensor (8B) that recognizes the recharge by RFID, TAG or microchip, and sends the recharge data to a PC that will be printed after the refilling, is automatically moved by a servo-motor (8E); the refilling system enabling the supplying of different chemical products that will be automatically recognized and pumped to the corresponding tank, wherein said method is applied in ambient disinfection, either in rooms or chambers, by vaporizing ozone or other chemical combinations suitable for sterilization or disinfection.

16. A method of use of an ozone sterilization or disinfection device with chemical products vapor injection wherein said device vaporizes and combines ozone with hydrogen peroxide, acetic acid, peracetic acid, water, formaldehyde or formaldehyde with water, through multiple capillary tubes (4D) in a vaporizer/mixer (4G) that feeds a sterilization/disinfection chamber (1), said feeding being made with a dose varying depending on the control performed by a computer or control unit, or being made with an adjustable dosing unit (13B); the vaporizer/mixer starts working with a pressure inferior to the atmospheric pressure and heated by an automatic and/or electrical system (4A), or by a microwave system (4J) at a temperature of 5° C. to 200° C.; the vaporization process being made in vacuum or at atmospheric pressure to a sterilization/disinfection chamber (1) at a pressure between 0.0001 mbar and 3000 mbar absolute: the filling of the chemical product, supplied from a tank (6F) is made drop by drop by capillary tubes (4D) with controlled temperature, which transform the liquid into a pulverized gas; the computer controlling electrical valves (4E and 4H) following the dosing pump (5) and ozone generator (12B) which includes a control board (12D) and an air entry filter (12C), taking into account the information concerning the pressure and/or temperature and/or humidity and/or concentration given by the sensors (1B, 2B, 3B, 4B and 11C), being the pressure inside the sterilization/disinfection chamber (1) maintained at a constant predefined value during the vaporization and sterilization or disinfection process; said device also comprising a vacuum pump (10A) which includes an exhaustion heating system (10N) and a temperature control sensor (10M) and an air valve heating system (10E) and a cooling system composed by an oil pump (10H) a heat dissipater (10I) a fan (10J) and an electronic control unit (10G), and also comprises a membrane (10Q) that separates the water from the oil, a liquid exhaustion system (10L), a liquids deposit (10O), an oil separator (10B) with connection to the air inlet (10F), and a molecular sieve (10C) with big a capacity between 0.5-5 L; at the exhaustion phase a plasma generator (9C) is activated to generate plasma by high voltage (9A) applied to the electrodes (9D), the temperature of the plasma generator being monitored by sensors (9E); the device comprising an automatic supplying system that removes the sterilizing agent from the bottle/container (8F) which is inserted in a holder (8G) that keeps said device in an inclined position that allows the perforation needle (8D) which is moved by a servo-motor (8C) to reach the bottom of the bottle/container and thereby remove the whole liquid, the drawer (8A) having a recharge recognition sensor (8B) that recognizes the recharge by RFID, TAG or microchip, and sends the recharge data to a PC that will be printed after the refilling, is automatically moved by a servo-motor (8E); the refilling system enabling the supplying of different chemical products that will be automatically recognized and pumped to the corresponding tank;

wherein said device performs the functions of a RESISTOMETER.

* * * * *